United States Patent [19]

Feibus

[11] Patent Number: 5,180,375
[45] Date of Patent: Jan. 19, 1993

[54] WOVEN SURGICAL DRAIN AND WOVEN SURGICAL SPONGE

[76] Inventor: Miriam H. Feibus, 2557 Morrocroft La., Charlotte, N.C. 28226

[21] Appl. No.: 694,748

[22] Filed: May 2, 1991

[51] Int. Cl.⁵ .............................................. A61M 5/00
[52] U.S. Cl. ................................. 604/264; 604/355; 604/282
[58] Field of Search ............... 604/255, 282, 264, 268, 604/3, 20, 28, 54, 290, 368, 369, 370; 66/195, 202; 428/253; 128/379–383, 362, 783, 799

[56] References Cited

U.S. PATENT DOCUMENTS

| | | | |
|---|---|---|---|
| 3,498,286 | 3/1970 | Polanyi et al. | 604/282 |
| 3,658,065 | 4/1972 | Hirsch | 604/355 |
| 3,957,054 | 5/1976 | McFarlane | 128/350 |
| 4,080,970 | 3/1978 | Miller | 128/350 |
| 4,139,012 | 2/1979 | Zahorsky | 128/350 |
| 4,217,904 | 8/1980 | Zahorsky | 128/350 |
| 4,257,422 | 3/1981 | Duncan | 128/350 |
| 4,296,855 | 10/1981 | Blalock | 428/255 |
| 4,315,509 | 2/1982 | Smit | 128/303 |
| 4,508,533 | 4/1985 | Abramson | 604/35 |
| 4,523,920 | 6/1985 | Russo | 604/93 |
| 4,551,141 | 11/1985 | McNeil | 604/317 |
| 4,579,555 | 4/1986 | Russo | 604/282 |
| 4,623,329 | 11/1986 | Drobish et al. | 604/29 |
| 4,654,032 | 3/1987 | Morales-George | 604/174 |
| 4,692,153 | 9/1987 | Berlin et al. | 604/171 |
| 4,753,088 | 6/1988 | Harrison et al. | 66/202 |
| 4,781,678 | 11/1988 | deCouët et al. | 604/45 |
| 4,815,299 | 3/1989 | Bryant | 66/202 |
| 4,856,299 | 8/1989 | Bryant | 66/202 |
| 4,970,109 | 11/1990 | Bryant | 428/253 |
| 5,053,021 | 10/1991 | Feibus | 604/264 |

*Primary Examiner*—Randy C. Shay
*Assistant Examiner*—G. Gualtieri
*Attorney, Agent, or Firm*—Kenyon & Kenyon

[57] ABSTRACT

The present invention relates to a surgical drain fabric and surgical drain device and surgical sponge for providing a channel of exit or discharge from a wound or wound cavity and, more specifically, a woven surgical drain fabric, woven surgical drains, and woven surgical sponges having finished longitudinal edges useful for drawing wound drainage out of a patient's body. Preferably, the surgical drain fabric, surgical drains, and surgical sponges are woven with conductive yarns and nonconductive yarns so as to provide enhanced drainage characteristics. The fabric, drains, and sponges prepared in accordance with the invention minimize the danger of sluffing and linting and other disadvantages associated with previous surgical drain and sponge materials.

15 Claims, 4 Drawing Sheets

WOVEN SURGICAL DRAIN AND WOVEN SURGICAL SPONGE

FIELD OF THE INVENTION

This invention relates to an appliance or material which provides a channel of exit or discharge from a wound cavity and, more specifically, to a woven surgical drain fabric and woven hollow-tube, hollow-track-tube, or hollow-flat-tube surgical drains comprised of electrically conductive yarns and nonconductive yarns that allows: the improved, i.e., more rapid and continuous removal of discharge from a wound cavity, improved removal of particulates from a wound cavity, and in the case of the hollow-tube or track-tube surgical drains, a conduit through which medication can be directly administered to the wound site. The surgical drains of this invention may also improve drain-off of particulate material suspended in the liquid to be drained.

The surgical drain fabric and the surgical drains of this invention, particularly the track-tube drain, when filled with an absorptive material, can also be folded, rolled wrapped or otherwise formed into a wad or sponge useful in medical procedures (especially dental procedures) for collecting and rapidly removing excess liquid such as blood or saliva.

BACKGROUND OF THE INVENTION

The therapeutic effect of promoting drainage from wound cavities is well known and there are conventional devices designed to promote such drainage. These devices which afford a route of exit or discharge from a wound cavity have come in various forms and can be classified generally in three groups.

The first group employs a hollow structure, such as a tube, which is placed in the wound to allow the removal of wound discharge by, e.g., capillary action and/or siphonage and/or gravity. A number of these "tube" type drains have also been used in conjunction with vacuum producing apparatus to assist drainage. Features shared by tube-type surgical drains include 1) ease of insertion into a wound cavity and 2) their drainage function is not generally affected by the volume of discharge. Further, since they provide constant drainage, the need to replace them is significantly reduced. There are, however, a number of disadvantages of tube-type surgical drains, including, the difficulties of avoiding infection and promoting healing inherent in a device inserted in a wound cavity that is nondegradable. Tube-type surgical drains can also be uncomfortable for the patient because of their stiffness, lack of flexibility, and relatively large diameter. In addition, tube-type surgical drains may be prone to blockage and other forms of obstruction, e.g., when the tube opening contacts body tissue the passage of discharge may be obstructed.

The second group of surgical drain devices includes those made of various forms of fibers and fabrics having absorptive properties which are placed in a wound cavity to allow removal of wound discharges, e.g., by absorption. Features shared by these "fabric" type surgical drains are that they can be relatively easily sized and manipulated regardless of the size of the wound cavity and may be less prone to blockage or obstruction than tube-type drains. As with tube-type drains, fabric-type drains suffer from a number of disadvantages, such as susceptibility to sluffing or linting, which may promote irritation and associated infection, and their drainage capacity may be limited to the fluid retention capacity of the fabric, i.e., the drainage is not continuous. Drainage capacity problems may be aggravated by using hydrophilic fibers, e.g., cellulose yarns, due to their water binding properties. A consequence of the drainage capacity limitation is that fabric-type surgical drains must ordinarily be replaced at relatively short intervals.

Further, conventional fabric-type drain materials are often so loosely woven that they fragment which increases the risk of infection. Natural fibers like cotton, and other cellulosics, are themselves prone to sluffing small fragments that also increase the risk of infection. Depending on the fibers selected, known fabric-type surgical drains may decompose over time, again necessitating more frequent replacement, and, not uncommonly, debriding of the wound cavity. Known fabric-type surgical may also be difficult to relocate or retrieve Another disadvantage of fabric-type drain materials is that they often do not remove particulates from the wound cavity.

The third group of surgical drain devices is a hybrid of the above described tube-type and fabric-type drains including both a hollow structure and absorptive fibers. In these combination-type surgical drains, a fabric is usually either wrapped around or arranged within a hollow structure to form a composite structure which may be inserted into a wound. Combination-type drains share some of the advantageous features of both tube-type and fabric-type drains. A disadvantage of these combination-type surgical drains is that they may not effectively remove particulates from a wound cavity.

An example of a combination-type drain routinely used in surgical procedures is made from gauze, e.g., a loosely woven cotton fabric, which may be layered, cut to size, shaped, and then placed in either surgical sheathing or a tubular part (finger) cut from a rubber glove prior to insertion into a wound cavity. The surgical sheathing or rubber glove part is used to prevent loose fragments or threads of the gauze from entering the wound cavity. Gauze is prone to fragmenting and leaves many loose threads when it is cut. Additional fragments of gauze may fall away under minimal pressure, i.e., sluffing and linting. The use of the sheath or glove to limit such sluffing and linting however, is not completely effective or convenient for use in an operating room setting. Furthermore, drainage with this type of surgical drain may be limited to the fluid retention capacity of the fabric and a small amount of evaporation.

Other known surgical drains, include "cigarette drains," made by surrounding a strip of gauze with a protective covering of rubber, gutta-percha, or the like; and "Mikulicz" drains formed by pushing a single layer of gauze into a wound cavity, the layer of gauze being packed with several thick wicks of gauze as it is pushed into the cavity. These drains also suffer from disadvantages including susceptibility to sluffing or linting, and that their drainage capacity may be limited to the fluid retention capacity of the fabric.

U.S. Pat. No. 3,957,054, issued to McFarlane, describes a tube-type drain which is flexible and pliable and comprises a plurality of ribs arranged in such a fashion about the interior of the column of the tube so that the tube cannot be collapsed.

U.S. Pat. No. 4,139,012, and its related continuation application, now U.S. Pat. No. 4,217,904, both issued to Zahorsky, describe surgical drain tubes having a construction said to minimize the problem of clogging found in known tube designs via a protective shield member.

Other known surgical drains are described in U.S. Pat. Nos. 4,257,422; 4,551,141; 4,623,329; 4,315,509; 4,579,555; 4,080,970; 4,781,678; 4,692,153; 4,523,920; 4,654,032; 4,508,533; 4,856,299; and 4,815,299.

A need exists, therefore, for a relatively inexpensive and easily manufactured surgical drain capable of providing improved drainage and other advantageous properties without some of the disadvantages of known surgical drains such as clogging, sluffing, linting, slow drainage, non-continuous drainage, inability to remove particulates, and inability to provide a conduit for administering medication directly to the site, and decomposition. Similarly, a desirable surgical drain fabric would provide improved continuous drainage properties for extended periods that is not limited to the fluid retention capacity of the fabric or evaporation time.

OBJECTS AND SUMMARY OF THE INVENTION

An object of the present invention is to provide a readily manufactured woven surgical drain fabric having finished edges which is comprised of a woven structure of conductive yarns and nonconductive yarns woven together so that the fabric has finished longitudinal edges and the conductive yarns make electrical contact with one another so as to form an electrically conductive matrix so as to form an electrically conductive woven matrix to provide absorptive properties without the sluffing or linting associated with known surgical drain fabrics.

It is another object of the present invention to provide a woven surgical drain fabric that can be sterilized by conventional processes and is comprised of conductive yarns and nonconductive yarns woven together and possesses a radio opaque means so that the resulting fabric is radiographically visible and thereby can be readily positioned and repositioned without further exploratory surgery or otherwise intrusive procedures.

It is another object of the present invention to provide a woven surgical drain comprising an elongate body defining a tube-like channel for fluids and particulates formed with conductive and nonconductive yarns woven together so that the surgical drain has a finished longitudinal edge and said conductive yarns make electrical contact with one another so as to form an electrically conductive woven matrix.

It is another object of the present invention to provide a woven surgical drain comprising conductive and nonconductive yarns woven together to form a woven hollow-cylindrical-tube, hereafter referred to as a woven hollow-tube, track-tube, or hollow-flat-tube surgical drains having finished longitudinal edges wherein the conductive yarns form an electrically conductive matrix. The matrix is not continuous except when stop-stitched.

It is another object of the present invention to provide a woven surgical drain comprising a hollow member whose shape and function can be varied by varying the shape, composition, and amount of a filler material disposed therein.

It is another object of the present invention to provide a surgical drain in the form of a woven surgical drain drawn through a plastic tube that is easy to use and provides improved, i.e., more rapid and continuous drainage, without the dangers of clogging, linting or sluffing.

It is another object of the present invention to provide for woven non-linting, highly compact, re-usable, and highly absorptive wads or sponges.

The invention also embraces methods for making and using both the surgical drain fabric and surgical drain described above.

The invention is described in greater detail below based on a few exemplified embodiments.

BRIEF DESCRIPTION OF THE DRAWINGS

The invention shall be further explained and described in the following text and accompanying drawings.

DETAILED DESCRIPTION OF THE INVENTION

Figure 1:
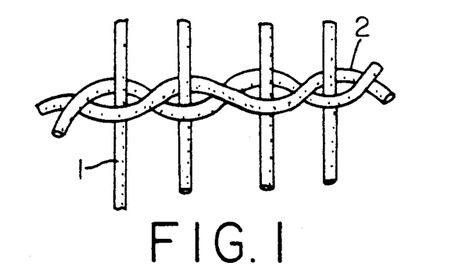
FIG. 1 shows a woven surgical drain fabric pattern illustrating the underlaps and overlaps of the weft and warp arrangement of a woven fabric, drain, or sponge woven in accordance with the present invention.

FIG. 1 shows a woven surgical drain fabric and the arrangement of underlaps and overlaps of warps 1 and wefts 2 formed in a fabric or surgical drain woven in accordance with the invention. For purposes of illustration only the warps 1 and wefts 2 are shown loosely woven together. In an actual woven fabric or surgical drain woven in accordance with the invention, the warps 1 and wefts 2 would be tightly woven together.

Figure 2:
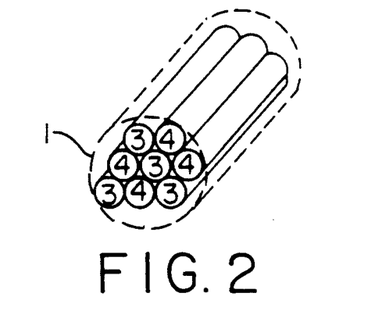
FIG. 2 shows a close-up cross-section of a warp of the surgical drain fabric shown in FIG. 1.

FIG. 2 is an enlargement of a warp 1 of FIG. 1 showing that the warp 1 is a multi-filament yarn comprised of approximately four conductive filaments ("yarn ends") 3 and four nonconductive filaments ("yarn ends") 4. Both warps 1 and wefts 2 may be comprised of any number of filaments. The characteristics of the woven fabric may be modified as needed by varying the type and denier of the warp yarn ends and weft yarn ends, the number of warps, and the number of picks per inch.

Figure 3:
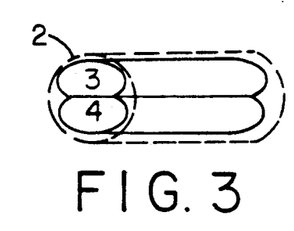
FIG. 3 shows a close-up cross-section of a weft of the surgical drain fabric shown in FIG. 1.

FIG. 3 is an enlargement of a weft 2 of FIG. 1 showing that the weft is comprised of approximately one conductive filament 3 and approximately one nonconductive filament 4.

Figure 4:
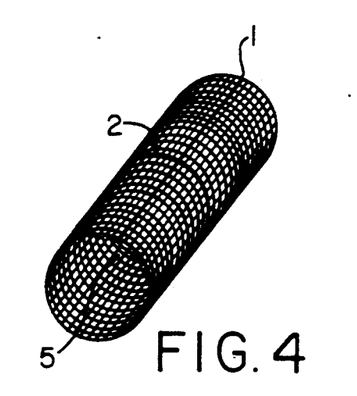
FIG. 4 shows a hollow-tube surgical drain.

FIG. 4 shows a hollow-tube surgical drain and includes warps 1, wefts 2, and a tube-like channel 5 for draining fluids and particulates.

Figure 5:
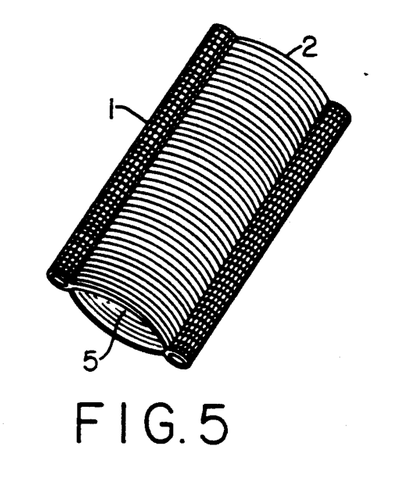
FIG. 5 shows a hollow-track-tube surgical drain made in accordance with the invention.

FIG. 5 shows a hollow-track-tube surgical drain and includes a plurality of laterally located warps 1, concentrated along the lateral edge of the channel and woven thereat with wefts 2, forming a tube-like channel 5 for draining fluids and particulates.

Figure 6:
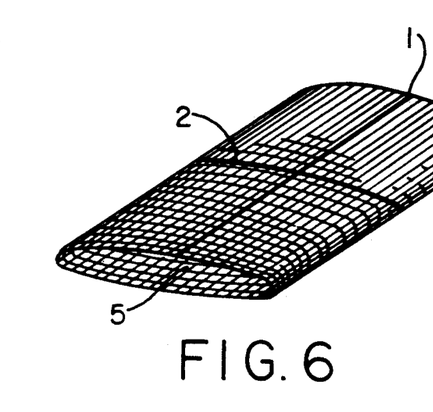
FIG. 6 shows a hollow-flat-tube surgical drain made in accordance with the invention.

FIG. 6 shows a hollow-flat-tube surgical drain and includes warps 1, wefts 2, and a tube-like channel 5 for draining fluids and particulates. The flat-tube-drain is woven so as to remain "flat" when there is a minimal amount of space or patient comfort is a major concern, e.g., when performing facial plastic surgery or draining skin ulcers.

Figure 7:
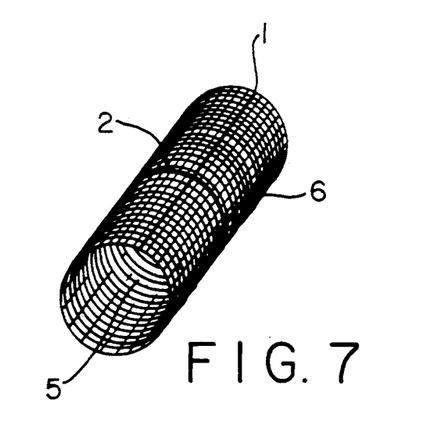
FIG. 7 shows the hollow-tube surgical drain shown in FIG. 4 with a stop-stitch.

FIG. 7 shows a hollow-tube surgical drain that includes warps 1, wefts 2, tube-like channel 5 for draining fluids and particulates, and a stop-stitch 6 sewn along the longitudinal edge of the drain parallel to the warps 1 and perpendicular to the wefts 2 to prevent continuous weft 2 unraveling.

Figure 8:
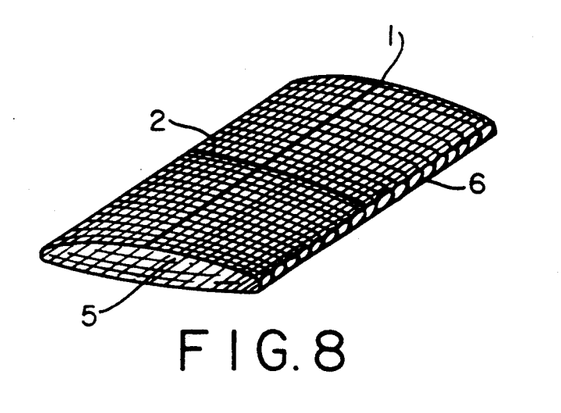
FIG. 8 shows the hollow-flat-tube surgical drain of FIG. 6 with a stop-stitch.

FIG. 8 shows a hollow-flat-tube surgical drain and includes warps 1, wefts 2, tube-like channel 5 for draining fluids and particulates, and a stop-stitch 6 sewn along the longitudinal edge of the drain parallel to the warps 1 and perpendicular to the wefts 2 to prevent continuous weft 2 unravelling.

Figure 9:
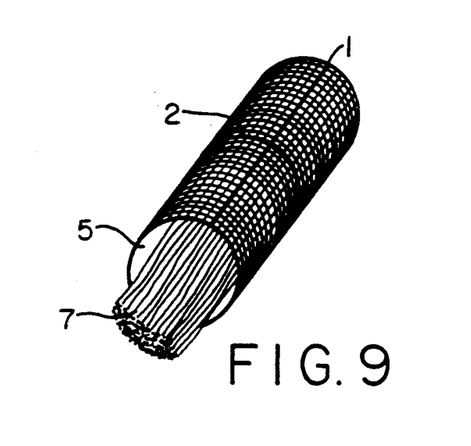
FIG. 9 shows a hollow-tube surgical drain with filler material.

FIG. 9 shows a hollow-tube surgical drain and includes warps 1, wefts 2, tube-like channel 5 for draining fluids and particulates, and a filler material 7 inserted into said tube-like channel 5. The filler cord 7 may be inserted as the hollow-tube drain is woven and allows the tube to maintain a desired shape while the drain is "finished" (for example by scouring, boiling, or heat setting). The shape of the drains, ranging from circular to flat, can be varied by the amount and shape of the filler cord inserted. After finishing, the filler material must be removed so as to form a drain. Alternatively, the filler cord may be comprised of absorptive fibers and left in place after finishing so as to form a sponge.

Figure 10:
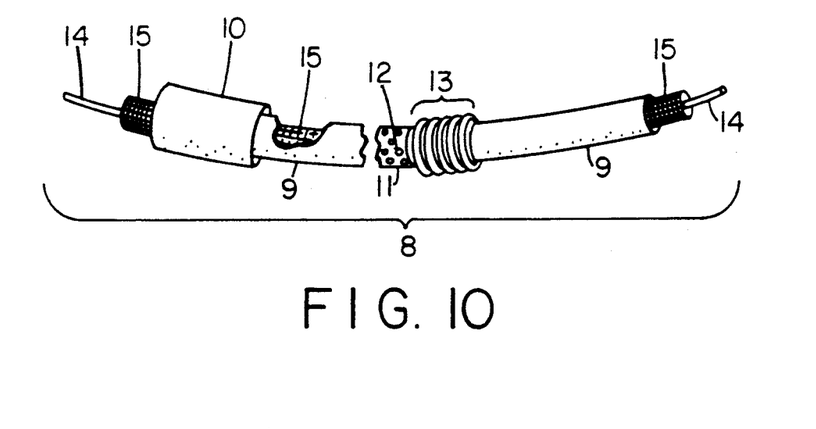
FIG. 10 illustrates a plastic hollow surgical drain having the surgical drain of the invention disposed therein.

FIG. 10 shows a surgical drain 8 which is a biocompatible plastic tube 9 preferably having a discharge connector 10 disposed at one end thereof for attachment to a drainage bag (not shown) or similar means for collecting wound drainage. Of course, discharge connector 10 could be attached to a vacuum assist device or simply left open. The opposing end 11 of tube 9 may be provided with perforations 12 to aid in collection of wound drainage. The tube 9 may be rigid or flexible, as dictated by particular applications, and may also include one or more flexing sections 13 to provide bending at desired locations. In addition, or alternatively, a bendable wire 14 can be passed through the tube 9 so that the drain 8 can be bent to any desired angle for selected applications. Preferably, the wire 14 is copper, silver, gold or other material having antimicrobial properties. It may also be advantageous to treat the surgical drain fabric 15 and/or tube 9 with known antimicrobial agents to reduce the risk of infection and/or to apply antithrombogenic agents to the tube 9, or portions thereof, such as heparin or sodium citrate.

Figure 11:
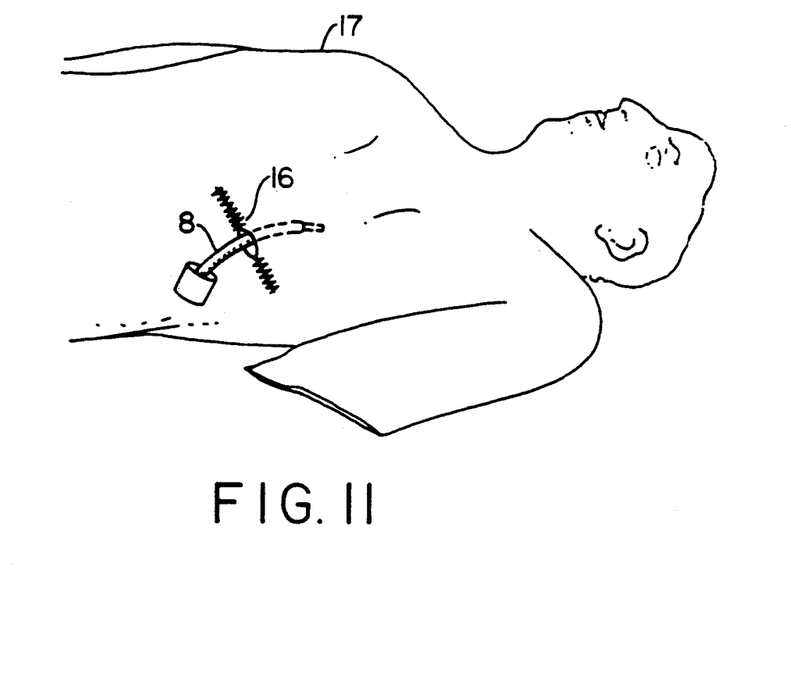
FIG. 11 illustrates a plastic hollow surgical drain (implanted in a wound) having a surgical drain of the invention disposed therein.

FIG. 11 shows surgical drain 8 extending from wound 16 in patient 17. The tube 9 which encloses the surgical drain fabric 15 can be made of any biologically acceptable material, synthetic plastics being preferred. The tube may be as rigid as a drinking straw or flexible as the finger of a latex surgical glove. Tube structures are easily formed by conventional plastic working processes such as extrusion. The tube would also provide a conduit through which medication can be directly administered to the site.

Figure 12:
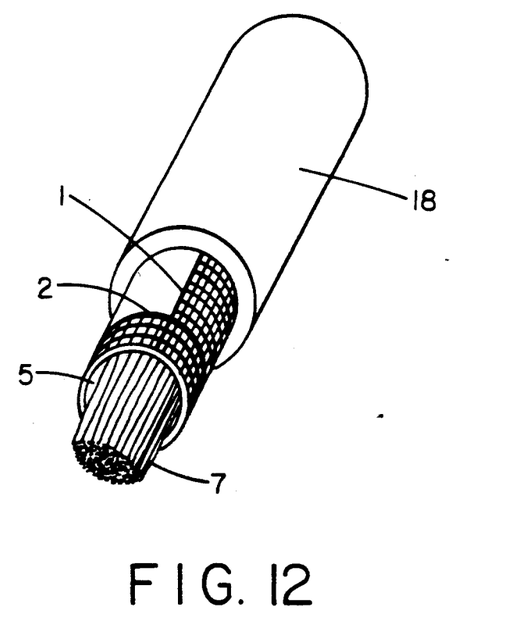
FIG. 12 shows the hollow-tube surgical drain of FIG. 9 encased by thermal sealing yarns.

FIG. 12 shows a hollow-tube surgical drain and includes warps 1, wefts 2, tube-like channel 5 for draining fluids and particulates, a filler cord 7 inserted into said tube-like channel 5, and thermal sealing fibers 18. The thermal sealing yarns 18 should have a lower melting point than the conductive and nonconductive yarns that comprise the warps 1 and wefts 2 of the drain. Thus, when the encased drain is exposed to sufficient heat to melt the thermal sealing yarns, the thermal sealing yarns will fuse into one another and the conductive and nonconductive yarns of the drain will be encased in a nonpermeable outer tube.

The sequence of woven yarns shown in FIG. 1 may be formed on a narrow loom knitting machine of the type well known in the art. Preferred machines for making surgical drain fabric and hollow-tube, hollow-track-tube, hollow-flat-tube surgical drains, and surgical sponges are weaving machines also capable of producing tubular woven fabrics with finished edges such as the "HIGH-CAPACITY NARROW-FABRIC LOOM (NF, NFS)" manufactured by Engineering Works Jakob Mueller Ltd., Frick, Switzerland. The material may also be produced on a braiding machine. The term finished edge means that the marginal edges of the fabric are substantially free of loose yarn ends that are susceptible to breaking away from the fabric. Those skilled in the art will appreciate that selvedging, bonding and similar known techniques can be employed to finish edges on alternative fabric constructions.

In accordance with the invention, a fabric or surgical drain useful for drawing wound drainage out of a patient's body should be woven from conductive and nonconductive fibers. Fabrics and drains woven using only nonconductive yarns are durable but do not produce acceptable drainage. Fabrics and drains woven using only conductive yarns produce acceptable drainage but tend to be fragile and expensive. Thus, a combination of conductive yarns and non-conductive yarns should be employed The ratio of conductive fibers to non-conductive fibers in the surgical fabrics and surgical drains prepared by Applicant is about 1:1, however, any ratio may be employed depending upon specific drainage and strength requirements.

It should be appreciated that the surgical drain fabric of this invention can be any knitted, woven or nonwoven material of staple or monofilament or multifilament yarns that includes an electrically conductive matrix and is woven to form a fabric that will provide effective wound drainage over extended periods of time, e.g., up to 2 or more days. The preferred form for the fabric is a hollow-tube, track-tube, or hollow-flat-tube having finished longitudinal edges. Hollow-tubes, track-tubes, or hollow-flat-tubes, can either be woven with finished edges or cut from sheets followed by finishing the edges. Preferably, the drain width is in the range of about 5 to 25 mm. A filler material may be temporarily or permanently inserted in the longitudinal opening of the drains depending upon whether a drain or a sponge is desired. One function of the filler cord is to shape the tube during final treatment or "finishing" (for example by scouring, boiling, or heat setting). After finishing, the filler cord may be removed leaving the drain in the desired shape. Alternatively, the filler material may be comprised of absorptive fibers and may be left in place after finishing if it is desired to make a sponge rather than a drain.

The nonconductive yarn used to make the surgical drain fabric of this invention can be any of the well known biocompatible yarns; and preferably is a monofilament or multifilament synthetic yarn such as a texturized polyester, e g., UNIFI 1-150-50, (20 to 200 denier). Polyesters are preferred because they are not easily degraded by body fluids or medicaments. Other available microfilament yarns, such as 1-150-100 and 1-150-256 available from DuPont TM and texturized by UNIFI may be advantageously incorporated in this product. Staple yarns should be avoided because small pieces of these yarns can sluff-off in use and may cause infection.

The conductive yarns are preferably monofilament or multifilaments made of any electrically conductive material, e.g., see: U.S. Pat. No. 4,422,483. Preferred conductive yarns are carbon suffused nylon yarn such as BASF TM ResiStat TM and the tri-lobal carbon core polyester yarn such as Dupont TM Nega-Stat TM. One advantage that Nega-Stat TM has over ResiStat TM is that Nega-Stat TM has a better radiographic signature than ResiStat TM. Fabrics and drains woven with Nega-Stat TM only as the conductive yarn drained more rapidly than fabrics and drains woven with ResiStat TM only as the conductive fiber. A disadvantage of fibers and drains woven with Nega-Stat TM only as the conductive yarn is that the rate of drainage is drastically reduced by the presence of oil in the fluid to be drained. Although fibers and drains prepared with ResiStat TM only as the conductive yarn drain more slowly and have a smaller radiographic signature, they are not affected by oil in the fluid to be drained. Thus, the Nega-Stat TM and the ResiStat TM perform better in concert than either does alone. The Nega-Stat TM and ResiStat TM may be utilized in any ratio, however, best results are obtained when the ratio of ResiStat TM to Nega-Stat TM is about 1:1. Other conductive fibers may also be utilized.

The conductive and nonconductive yarns may also be encased in thermal sealing yarns. The use of thermally sealed yarns to encase the conductive an nonconductive yarns of the surgical drains results in more rapid removal of discharge from a wound cavity and provides a conduit through which medication can be directly administered to the site.

The surgical drain fabric and the surgical drains of this invention, particularly the track-tube drain, when prepared with an absorptive filler material can also be folded, rolled, wrapped, or otherwise formed into a wad or sponge useful in medical procedures, especially dental procedures, for collecting and rapidly draining excess liquid such as blood or saliva. The surgical drains of this invention will also drain off particulate material suspended in the liquid to be drained.

EXAMPLE 1

An example of a non-linting and non-sluffing woven surgical drain fabric of the present invention was woven on a narrow loom machine. The woven weft and warp yarns of the conductive fibers form an electrically conductive matrix. The woven pattern is important because the woven pattern provides finished edges and, as previously discussed, the lack of loose threads reduces the chance of infection.

The result of the above procedure is a finished edge surgical drain fabric or finished edge hollow-tube, track-tube, or hollow-flat-tube surgical drain that has a diameter of approximately ⅜" (7.5 mm) and can be made into any desired length. The woven surgical drain fabric or woven hollow-tube, track-tube, or hollow-flat-tube surgical drains of the present invention may then be treated by the steps of:
1. "finishing", i.e., scouring or boiling; and
2. heat setting the scoured fabric or drains at about 350 degrees Fahrenheit.

As will be appreciated, a benefit of the woven patterns of the present invention is that no additional mechanical finishing, e.g., sewing or burning, of the fabric's edges is needed to bind loose threads.

In order to achieve wider hollow-tube, track-tube, or hollow-flat-tube surgical drains (up to two inches (2") in diameter), the same loom machine can be utilized in substantially the same manner as described but would require more creel space. For widths greater than one-and-one-quarter (1¼") inches diameter a modified loom should be employed.

EXAMPLE 2

It has also been discovered that a hydrophobic fabric, such as that used in the present invention, can drain more quickly, i.e., begin to move blood sooner if the fabric is pre-wet with a liquid such as, for example, water or mixtures of water and alcohol or heprin particularly 1 to 5% vol. aqueous isopropyl (rubbing) alcohol. In a preferred embodiment, the fabric or drain is pre-wetted with an alcohol-water solution.

Tap water was used to wet woven surgical drains constructed in accordance with the present invention. Three samples of a hollow-tube surgical drain were prepared with each drain having a diameter of approximately 7 mm and measuring approximately 17 cm in length. Drain No. 1 was totally immersed in the tap water so that it became soaked; Drain No. 2 was only dampened; and Drain No. 3 was dry.

In the first test "A", 250 cc of Povidone TM iodine prep solution (which is quite viscous and has a tendency to dry rapidly) was placed in three separate coupe shaped containers. One end of each woven hollow-tube surgical drain was submerged in the Povidone and the opposite end draped over the side of the glass tube into a collection vessel. The collecting vessel was placed lower than the vessel containing the liquid to be drained. The volume of liquid in each collection vessel was periodically measured and the results are summarized in Table I.

In the second test "B", the woven hollow-tube surgical drains were wet with tap water. Drain 1 was soaked; Drain 2 was only dampened; and Drain 3 was dry. The three sample Drains were used to drain Povidone TM as in Test A and the results are also summarized in Table I, wherein the cumulative amount of fluid drained (in milliliters) over a given period is illustrated.

TABLE I

| Drain | 2 minutes | 180 minutes | 240 minutes | 270 minutes |
|---|---|---|---|---|
| A. Povidone TM iodine prep solution. | | | | |
| 1. | 200 ml | 250 ml | — | — |
| 2. | 100 ml | 250 ml | — | — |
| 3. | 0 ml | 150 ml | 225 ml | 250 ml |

| Drain | 2 minutes | 15 minutes | 30 minutes | 70 minutes |
|---|---|---|---|---|
| B. Sterilized water. | | | | |
| 1. | 200 ml | 250 ml | — | — |
| 2. | 200 ml | 250 ml | — | — |

TABLE I-continued

| 3. | 0 ml | 50 ml | 100 ml | 250 ml |
| --- | --- | --- | --- | --- |

The effects of soaking, dampening, and leaving the surgical drain dry as summarized in Table I demonstrate that the most rapid drainage occurs when the drain is either pre-soaked or pre-dampened instead of being merely left dry.

EXAMPLE 3

A hollow track-tube surgical drain approximately 17 cm long and having a diameter of approximately 7 mm was prepared in accordance with the invention. The drain was pre-soaked with tap water. The drain was used to drain 75 ml of sterilized water from a 75 ml beaker. The collecting vessel was placed lower than the vessel containing the liquid to be drained. The results are summarized in Table II.

TABLE II

| DRAINAGE RATE FOR HOLLOW-TRACK-TUBE SURGICAL DRAIN | | | |
| --- | --- | --- | --- |
| | 5 minutes | 15 minutes | 29 minutes |
| $H_2O$ DRAINED | 40 ml | 50 ml | 75 ml |

EXAMPLE 4

A flat-tube surgical drain approximately 17 cm long and having a diameter of approximately 7 mm was prepared in accordance with the invention. The drain was pre-soaked with tap water. The drain was used to drain 75 ml of tap water from a 75 ml beaker. The collecting vessel was placed lower than the vessel containing the liquid to be drained. The results are summarized in Table III.

TABLE III

| DRAINAGE RATE FOR HOLLOW-FLAT-TUBE SURGICAL DRAIN | | | | | |
| --- | --- | --- | --- | --- | --- |
| 5 minutes | 15 minutes | 29 minute | 50 minutes | 75 minutes | 150 minutes |
| 30 ml | 35 ml | 50 ml | 62 ml | 70 ml | 75 ml |

$H_2O$ DRAINED

The drainage properties of the pre-soaked hollow-track-tube and hollow-flat-tube surgical drains as summarized in Tables II and III demonstrate that the hollow-track-tube drain drains more rapidly than the hollow-flat-tube drain.

EXAMPLE 5

Three surgical sponges were prepared in accordance with the invention. A first surgical sponge was prepared by preparing a hollow-tube surgical drain in accordance with the invention having a length of approximately 2.5 cm and a diameter of approximately 7 mm. This hollow-tube surgical drain was filled with 100 ends of UNIFI 1-150-68 texturized polyester. A second surgical sponge was prepared using a section of hollow-tube surgical drain prepared in accordance with the invention and having the same dimensions as the drain prepared for the first surgical sponge. The second hollow-tube surgical drain was filled with 100 ends of UNIFI 1-150-68 texturized polyester and 100 ends of ResiStat TM. A third surgical sponge was prepared using a section of hollow-tube surgical drain prepared in accordance with the invention and having the same dimensions as the drain prepared for the first and second sponges. The third hollow-tube surgical drain was filled with 150 ends of UNIFI 1-150-68 texturized polyester and 150 end of ResiStat TM. The sponges were placed in a container containing 40 cc of $H_2O$ to determine their absorption rates. The first surgical sponge absorbed 5 cc of $H_2O$, the second sponge absorbed 30 cc of $H_2O$ and the third sponge absorbed 40 cc of $H_2O$. The results are summarized in Table IV.

TABLE IV

| $H_2O$ ABSORPTION FOR SURGICAL SPONGES | |
| --- | --- |
| SPONGE | $H_2O$ ABSORBED |
| 1 | 5 cc |
| 2 | 30 cc |
| 3 | 40 cc |

The absorptive properties of surgical sponges as summarized in Table IV demonstrate that absorption properties are enhanced by including conductive fibers and increasing the number of yarn ends and/or varying the yarn types in the filler material.

It should be appreciated that the woven surgical drain fabric or hollow-tube, hollow-track-tube, or hollow-flat-tube woven surgical drains and surgical sponges of the present invention may be autoclaved and gamma ray sterilized and may be hypoallergenic depending on the choice of material used to make the fabric and/or tube. In addition, were the fabric or drains to be enclosed in a surgical sheath, the physician would have the flexibility to increase or decrease the rapidity of drainage, or even change the drain altogether from outside the patients body.

It should be understood that this invention is not limited to the illustrations described and shown herein, which are deemed to be merely illustrative of various modes of carrying out the invention. As will be appreciated by those skilled in the art, an infinite combination of woven patterns, shapes, sizes, and fillers is possible.

What is claimed is:

1. A woven surgical sponge which comprises: a first plurality of yarns and a second plurality of yarns, the yarns of said first plurality of yarns being substantially parallel to each other and extending in a first direction, the yarns of said second plurality of yarns being substantially parallel to each other and extending in a second direction substantially perpendicular to said first direction and woven with said first plurality of yarns to form an elongate woven fabric defining a tube-like channel and wherein said first plurality of yarns and said second plurality of yarns include conductive and nonconductive yarns and said conductive yarns make electrical contact with one another so as to form an electrically conductive matrix and an absorptive filler material inserted in said tube-like channel.

2. The sponge of claim 1 wherein the tube-like channel is in hollow-tube form.

3. The sponge of claim 1 wherein the tube-like channel is in track-tube form.

4. The sponge of claim 1 wherein the tube-like channel is in hollow-flat-tube form.

5. The sponge of claim 1 wherein said nonconductive yarns are synthetic yarns.

6. The sponge of claim 5 wherein said synthetic yarns are 1-150-50 polyester yarn.

7. The sponge of claim 5 wherein the synthetic yarns are 1-150-256 polyester yarns.

8. The sponge of claim 1 wherein said conductive yarns consist of two or more conductive yarns plied together.

9. The sponge of claim 1 wherein said conductive yarns consist of a conductive yarn plied together with a nonconductive yarn.

10. The sponge of claim 1 wherein said conductive yarns are chosen from the group consisting of carbon suffused nylon; filamentary polymer substrates having finely divided electrically-conductive particles embossed on the yarn surface; and graphite yarns.

11. The sponge of claim 1 wherein said conductive yarns are selected from the group consisting of carbon suffused nylon and tri-lobal carbon care polyester.

12. The sponge of claim 1 wherein said conductive yarns consist of carbon suffused nylon and tri-lobal carbon core polyester.

13. The sponge of claim 12 wherein the ratio of carbon suffused nylon yarns to tri-lobal carbon core polyester yarns is about 1:1.

14. The sponge of claim 1 wherein the ratio of conductive yarns to nonconductive yarns is about 1:1.

15. The sponge of claim 1 further comprising a lock-stitch on at least one of said longitudinal edges.

* * * * *